(12) United States Patent
Cutrone et al.

(10) Patent No.: US 6,291,461 B1
(45) Date of Patent: Sep. 18, 2001

(54) STEPHACIDIN ANTITUMOR ANTIBIOTICS

(75) Inventors: Jingfang Qian Cutrone, Wallingford; Kimberly D. Krampitz, Southington; Yue-Zhong Shu, Cheshire; Li-Ping Chang, New Britian; Susan E. Lowe, Cheshire, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/391,131

(22) Filed: Sep. 7, 1999

Related U.S. Application Data

(63) Continuation-in-part of application No. 09/329,151, filed on Jun. 9, 1999, now abandoned

(60) Provisional application No. 60/088,723, filed on Jun. 10, 1998.

(51) Int. Cl.[7] .................................................. A61K 31/495
(52) U.S. Cl. .............................. 514/252.11; 514/254.01; 544/338; 544/339
(58) Field of Search .................................. 544/338, 339; 514/252.11, 254.01

*Primary Examiner*—Amelia Owens
(74) *Attorney, Agent, or Firm*—David M. Morse

(57) ABSTRACT

The novel antitumor antibiotics designated stephacidin A and stephacidin B are produced by fermentation of *Aspergillus ochraceus* ATCC-74432. The antibiotics inhibit the growth of mammalian tumors, including particularly prostate carcinoma.

5 Claims, 8 Drawing Sheets

STEPHACIDIN ANTITUMOR ANTIBIOTICS

CROSS-REFERENCE TO RELATED APPLICATION

This application is a continuation-in-part of U.S. application Ser. No. 09/329,151 filed Jun. 9, 1999 now abandoned, which claims the benefit of U.S. Provisional Application Ser. No. 60/088,723 filed Jun. 10, 1998.

BACKGROUND OF THE INVENTION

1. Field of the Invention

This invention relates to novel antitumor antibiotics, designated by the present inventors as stephacidin A and stephacidin B, which may be obtained by cultivation of a strain of *Aspergillus ochraceus*. The antibiotics provided by the present invention are useful in inhibiting tumors in mammals.

2. Background Art

The present inventors are not aware of any literature disclosing stephacidin A or B or any compounds closely related in structure.

SUMMARY OF THE INVENTION

The present invention provides the novel antibiotics designated by the present inventors as stephacidin A and stephacidin B and a fermentation process for production of these antibiotics using a novel strain of *Aspergillus ochraceus* designated herein as *Aspergillus ochraceus* WC76466 (ATCC-74432). The antibiotics of the present invention have been found to be useful for the inhibition of tumors, particularly prostate carcinoma, in mammals.

Also provided are pharmaceutical compositions of stephacidin A and B, methods for the inhibition of mammalian tumors using the antibiotics of the present invention and processes for obtaining the antibiotics, including substantially purified forms thereof.

DETAILED DESCRIPTION OF THE INVENTION

Figure 1:
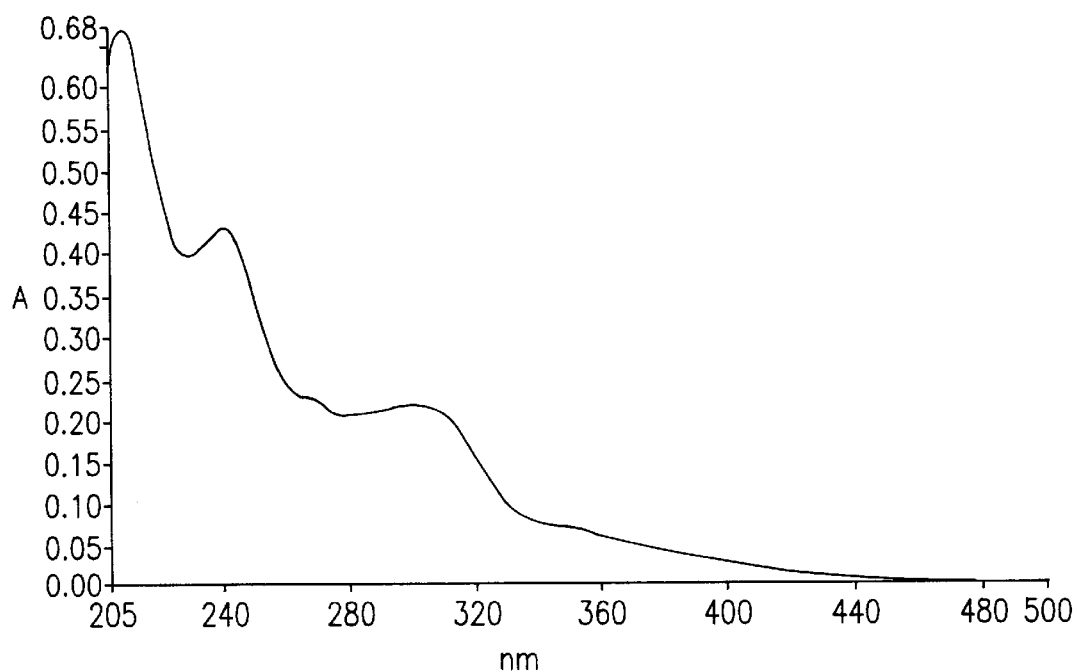
FIG. 1 shows the ultraviolet absorption spectrum of stephacidin B in methanol.

The preferred producing strain for production of stephacidins A and B is a mitosporic fungus, *Aspergillus ochraceus*, isolated from light brown clay collected from Sirsaganj, Uttar Pradesh, India.

In agar culture, colonies of the fungus exhibit the following cultural morphological characteristics:

Taxonomy of the Microorganism

Colonies on Cornmeal agar (Difco Laboratory) growing moderately fast, attaining 45–55 mm in diameter after 14 days at 25° C., 12 hr. photoperiod. Colonies effuse, immerse, translucent, and zonate. Sporulation relatively sparse. Spore mass appears Warm-Buff (XX) to Pale Orange Yellow (III) (capitalized color names from Ridgway, R. 1912. Color Standards and Nomenclature, Washington, D.C.). Reverse uncolored. Diffusible pigment none. Colorless exudates present. Odor present but not distinct.

Colonies on YMEA (malt extract 1%, yeast extract 0.2%, w/w) growing fast, attaining 60–73 mm in diameter after 14 days at 25° C., 12 hr. photoperiod. Colonies plane, effuse to lanose, and zonate. Mycelium hyaline. Sporulation moderate. Spore mass appear Pale Orange Yellow (III), Warm-Buff (XV), Colonial Buff (XXX) to Deep Colonial Buff (XXX). Reverse Chamois (XXX), Cream-Buff (XXX), Light-Buff (XV) to Pale Ochraceous-Buff (XV). Diffusible pigment none. Colorless exudates present. Odor present but not distinct.

Colonies on PDA (Difco Laboratory) growing fast, attaining 70–80 mm in diameter after 14 days at 25° C., 12 hr. photoperiod. Colonies effuse, and zonate. Mycelium white to Sea-foam Yellow (XXXI). Sporulation heavy. Spore mass appear Warm-Buff (XV), Cream-Buff (XXX), Chamois (XXX), Olive-Ocher (XXX), to Deep Colonial Buff (XXX). Reverse Cream Buff (XXX), Isabella Color (XXX), Natal Brown (XL), Light Buff (XV) to Light Seal Brown (XXXIX). Diffusible pigment none. Colorless exudates present. Odor present but not distinct.

Colonies on oatmeal agar growing very fast, attaining over 85 mm in diameter 25° C., 12 hr. photoperiod after 14 days at 25° C., 12 hr. photoperiod. Sporulation heavy. Spore mass appear Honey Yellow (XXX). Reverse color center Deep Olive-Buff (XL) to edge Dark Olive-Buff (XL). Diffusible pigment and odor none. Colorless exudates present.

Colonies grow very fast on DG18 (Samson, R. A. et al. 1995. Introduction To Food-Borne Fungi. Centraalbureau voor Schimmelcultures, Baarn, The Netherlands. pp.308–312.), attaining over 85 mm in diameter after 14 days at 25° C., 12 hr. photoperiod. Colonies lanate. Sporulation heavy. Spore mass appear Honey Yellow (XXX). Reverse Isabella Color (XXX). Diffusible pigment, exudates and odor none.

The producing culture WC76466 has globose conidial head when young, spilt into 2–3 divergent compact columns in age. Conidiophores rise from substrate mycelium, commonly 650–1300 µm in length, occasionally to 2000 µm, by 10–15 µm in diameter, occasionally to 20 µm, thick-walled (1–2 µm), dull yellow to yellowish-brown shades, upper two third coarsely roughened, appearing bumpy, lower portion smooth-walled, not constricted beneath the vesicle. Vesicles globose, occasionally subglobose, thick-walled, 35–50 µm in diameter, occasionally to 60 µm. Sterigmata covering entire vesicle, crowded, predominant biseriate, occasionally uniseriate; metula mostly wedge-shaped 12–20 µm by 5–7 µm but occasionally less than 10 µm in length, occasionally becoming septate; phialides 8–10 µm by 2–3 µm, 5–6 in a whirl on metula. Conidia globose to subglobose, hyaline to very light brown, thin-walled, smooth to finely roughened, 2–3.5 µm in diameter mostly 2.5–3.0 µm. Sclerotia not present.

A biologically pure culture of *Aspergillus ochraceus* strain WC76466 has been deposited with the American Type Culture Collection, 10801 University Boulevard, Manassas, Va. 20108-1549, under the accession number ATCC-74432.

As in the case of other producing microorganisms, the characteristics of the new stephacidin A and B-producing culture of the present invention, *Aspergillus ochraceus* ATCC-74432, are subject to variation. Recombinants, variants and mutants of the ATCC-74432 strain may be obtained by treatment with various known mutagens such as ultraviolet rays, X-rays, high frequency waves, radioactive rays, and chemicals. Natural and induced variants, mutants and recombinants of *Aspergillus ochraceus* ATCC-74432 which retain the characteristic of producing stephacidin A and B are intended to be encompassed by the present invention.

The stephacidin A and B antibiotics may be produced by cultivating a stephacidin A and B-producing strain of *Aspergillus ochraceus*, preferably *Aspergillus ochraceus* ATCC-74432 or a mutant or variant thereof, under submerged aerobic conditions in an aqueous nutrient medium. The fermentation is carried out until a substantial amount of stephacidin A and B are detected in the broth and then the desired antibiotics are harvested by extracting the active components from the mycelial growth with a suitable solvent. The solution containing the desired component(s) is concentrated and then the concentrated material subjected to chromatographic separation to isolate the component(s) in purified form substantially free of other co-produced materials.

The producing organism is grown in a nutrient medium containing an assimilable carbon source, for example an assimilable carbohydrate. Examples of suitable carbon sources include glucose, fructose, mannose, maltose, galactose, mannitol, glycerol, other sugars and sugar alcohols, starches and other carbohydrates, or carbohydrate derivatives such as dextran or cerulose, as well as complex nutrients such as oat flour, corn meal, millet, and the like. The exact quantity of carbon source which is utilized in the medium will depend in part upon the other ingredients in the medium, but it is usually found that an amount of carbohydrate between 0.5 to 10 percent by weight of the medium is satisfactory. The carbon sources may be used individually or several such carbon sources may be combined in the same medium.

The nutrient medium should also contain an assimilable nitrogen source such as amino acids (e.g. glycine, arginine, threonine, methionine and the like), ammonium salts, or complex nitrogen sources such as yeast extracts, corn steep liquors, distiller solubles, soybean meal, cottonseed meal, fish meal, and the like. The nitrogen source may be used alone or in combination in amounts ranging from 0.05 to 5 percent by weight of the medium.

Nutrient inorganic salts may also be incorporated in the medium and such salts may comprise any of the usual salts capable of providing sodium, potassium, magnesium, calcium, phosphate, sulfate, chloride, carbonate, and like ions. Trace metals such as cobalt, manganese, iron, molybdenum, zinc, cadmium, and the like may also be used if desired.

Production of the stephacidin antibiotics may be effected at any temperature conducive to satisfactory growth of the organism, i.e. approximately 18–45° C., and is conveniently carried out at a temperature of about 28° C. The fermentation may be carried out in flasks or in laboratory or industrial fermentors of various capacities. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium for large scale production of the desired antibiotic. The medium in which the vegetative inoculum is produced can be the same as, or different from, that utilized in the tank for the production of the new antibiotic as long as it is such that a good growth of the microrganism is obtained.

Figure 9:
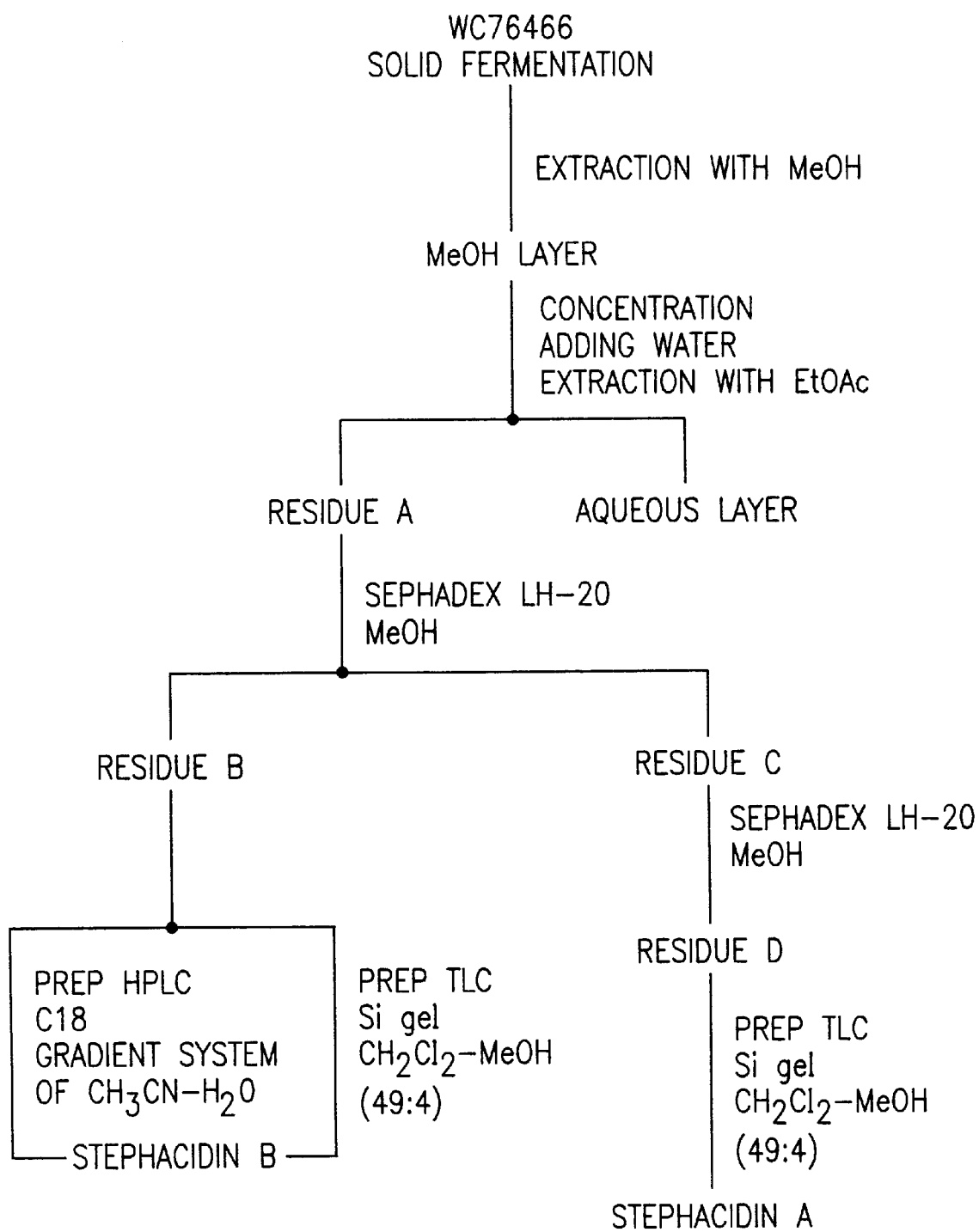
FIG. 9 shows the isolation scheme of stephacidin A and stephacidin B.

When fermentation is complete, stephacidin A and B are recovered from the fermentation broth and separated from co-produced substances and other impurities by art-recognized techniques. A typical isolation procedure is shown in FIG. 9 and in the example which follows.

The physico-chemical properties of stephacidin A and B are as follows:

TABLE 1

Physico-Chemical Properties of Stephacidin B

Figure 2:
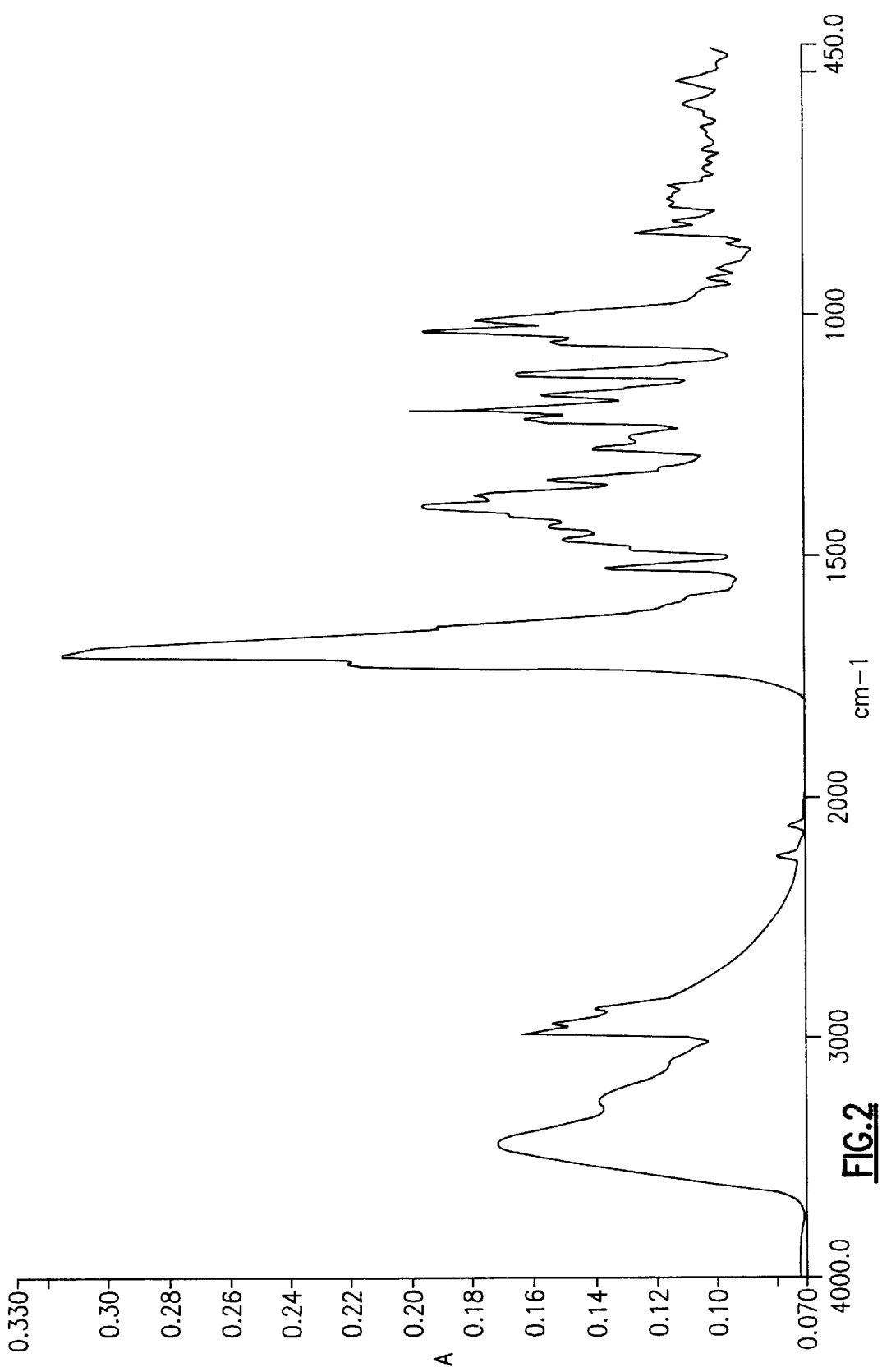
FIG. 2 shows the infrared absorption spectrum of stephacidin B (KBr pellet).
Figure 3:
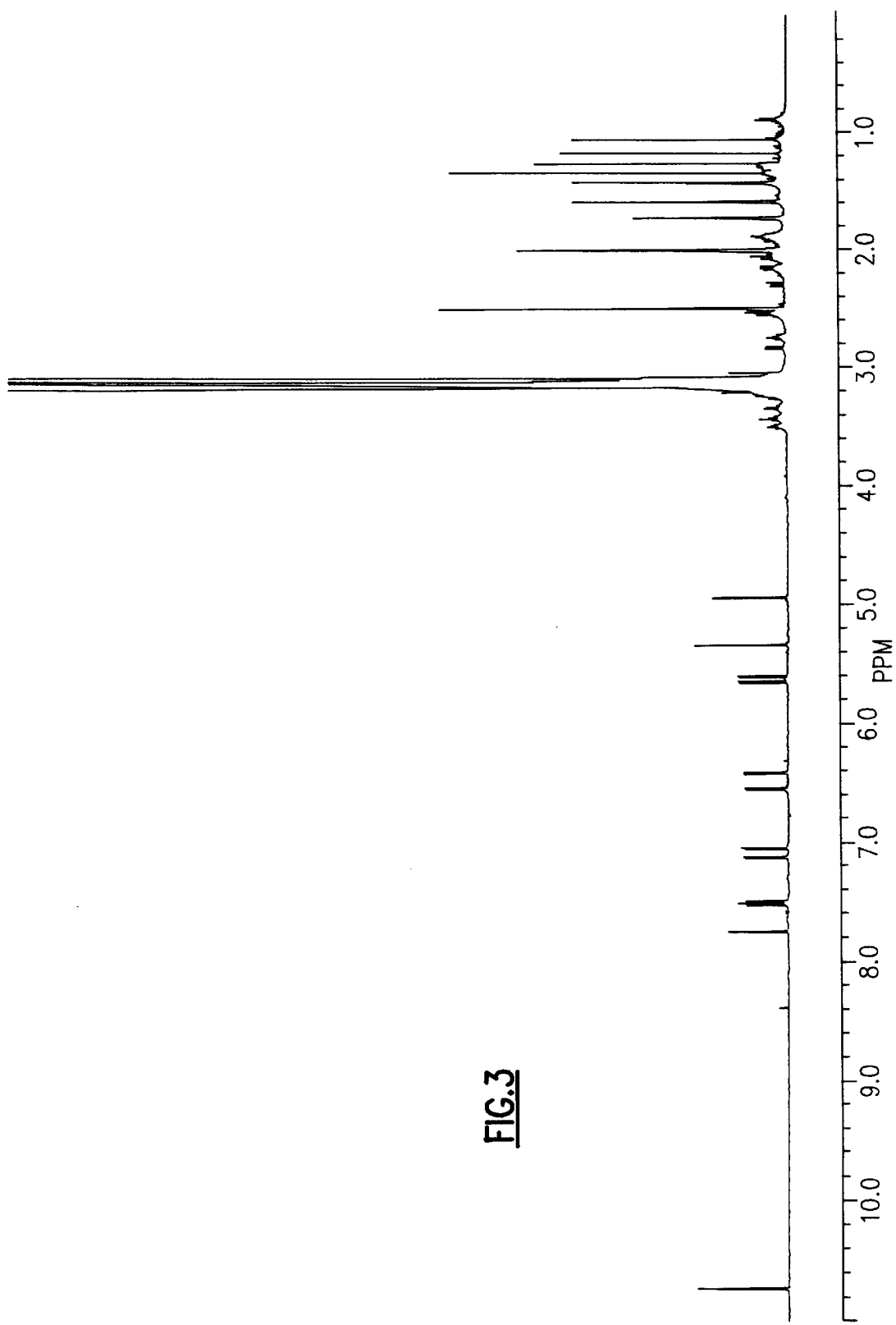
FIG. 3 shows the $^1$H-NMR spectrum of stephacidin B in DMSO/CD$_3$CN (1:1).
Figure 4:
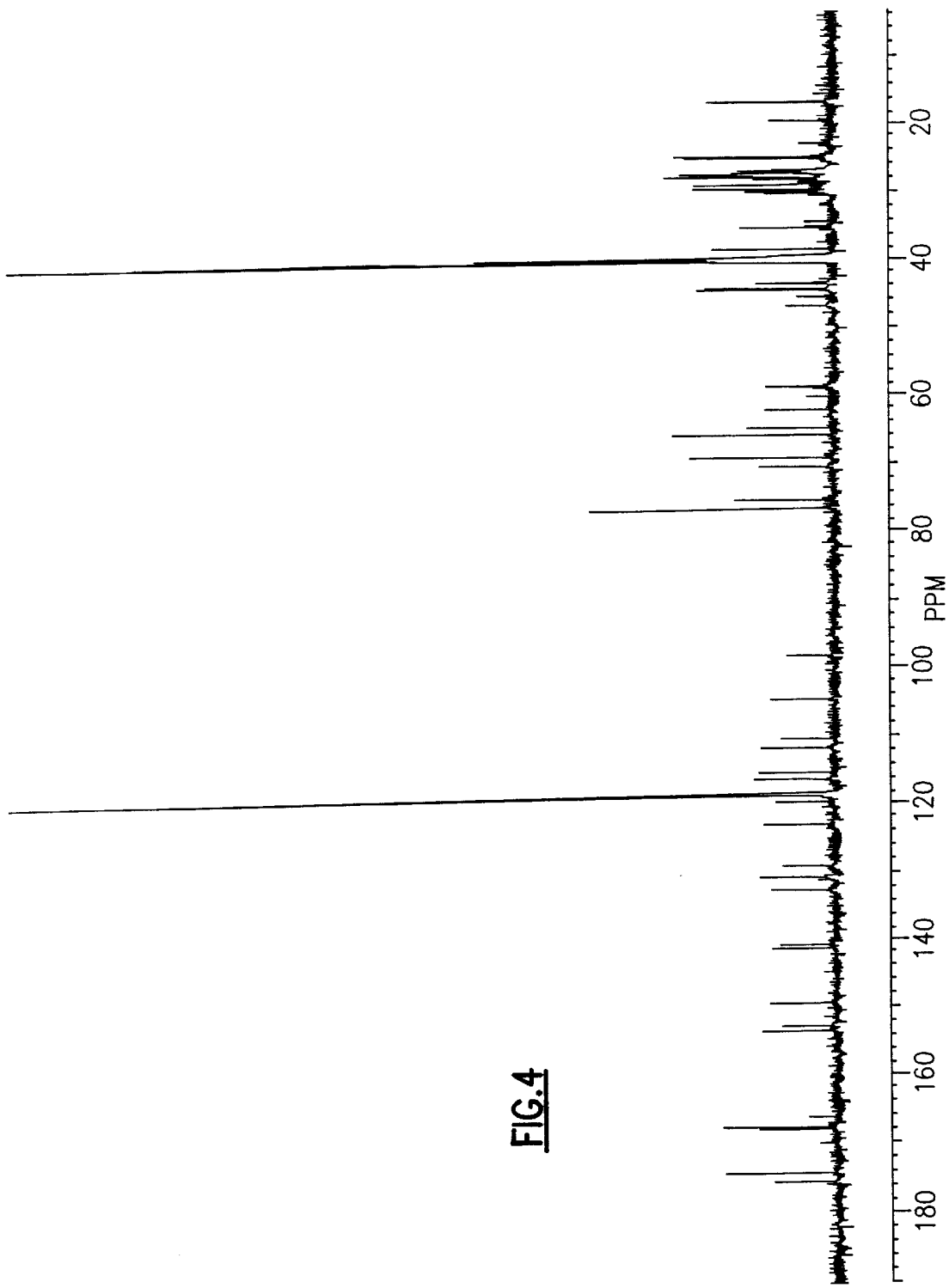
FIG. 4 shows the $^{13}$C-NMR spectrum of stephacidin B in DMSO/CD$_3$CN (1:1).

| | |
|---|---|
| Description: | Off-white amorphous solid |
| Solubility: | Soluble in methanol, chloroform, acetone, acetonitrile, dimethyl sulfoxide, and the solvent mixture ot acetonitrile/methanol (1:1), but insoluble in hexane and water. |
| Molecular Formula: | $C_{52}H_{54}O_8N_6$ |
| Molecular Weight: | 890 |
| Mass Spectrum: | HR-ESIMS ion: 891.4085 $[M + H]^+$ Positive ESI-MS ions: 891 $[M + H]^+$, 1781 $[2M + H]^+$ Negative ESI-MS ions: 889 $[M - H]^-$, 1779 $[2M - H]^-$ |
| Ultraviolet Spectrum: | $\lambda$ $max_{MeOH}$ (log $\epsilon$) 209 (4.73), 240 (4.54), 268 (sh. 4.27) 301 (4.26), 346 (sh. 3.79) nm (FIG. 1). Sample dissolved in methanol at concentration of 0.0011 g/L. |
| Infrared Spectrum: | Major Bands ($cm^{-1}$) 3429, 2972, 1713, 1683, 1671, 1638, 1520, 1459, 1386, 1337, 1276, 1210, 1190, 1162, 1115, 1025, 1004, 826, 757, 563, 510 $cm^{-1}$ (FIG. 2) |
| $^1$H-NMR | FIG. 3, in DMSO-$CD_3CN$ (1:1) |
| $^{13}$C-NMR | $\delta_C$ (DMSO—$CD_3CN$ 1:1) in ppm (FIG. 4) 175.1, 173.8, 167.5, 167.0, 153.0, 152.2, 148.8, 140.9, 140.2, 132.2, 130.4, 130.2, 128.6, 122.9, 119.5, 118.6, 116.2, 116.1, 115.3, 111.7, 110.3, 104.5, 98.0, 76.3, 75.2, 70.2, 68.9, 65.7, 64.7, 61.9, 58.5, 46.5, 44.3, 44.0, 43.3, 43.2, 38.2, 35.0, 29.8, 29.4,28.6, 28.0, 27.7, 27.2, 27.0, 26.7, 26.6, 26.3, 24.9, 24.5, 19.4, 16.3 |

TABLE 2

Physico-Chemical Properties of Stephacidin A

Figure 5:
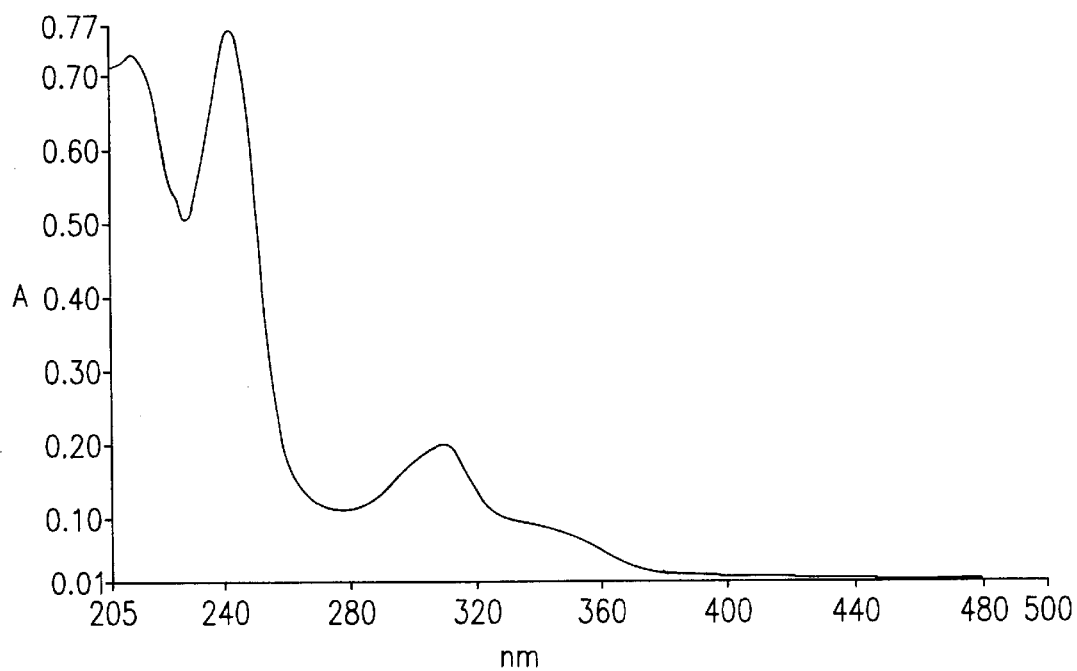
FIG. 5 shows the ultraviolet absorption spectrum of stephacidin A in methanol.
Figure 6:
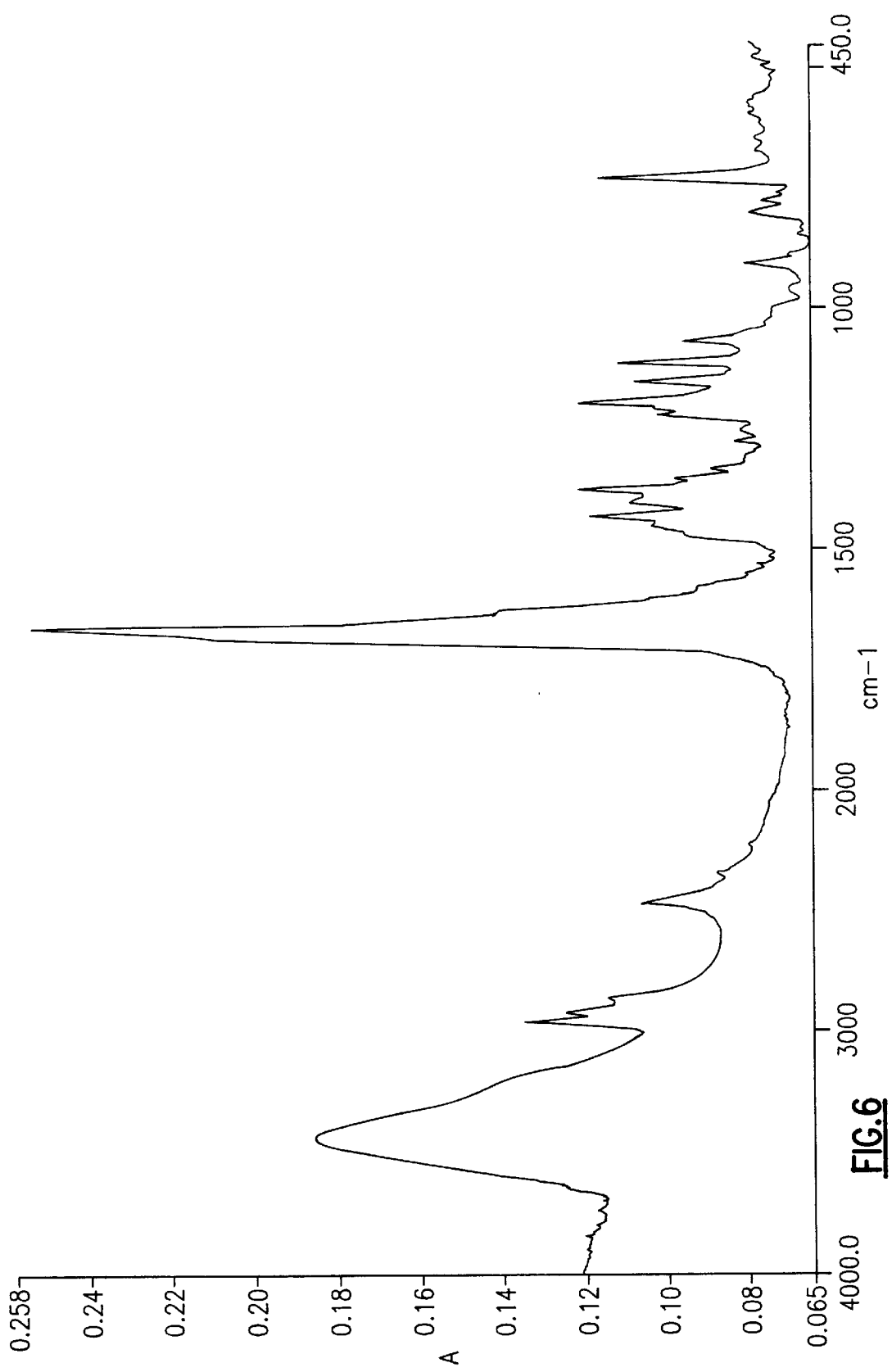
FIG. 6 shows the infrared absorption spectrum of stephacidin A (KBr pellet).
Figure 7:
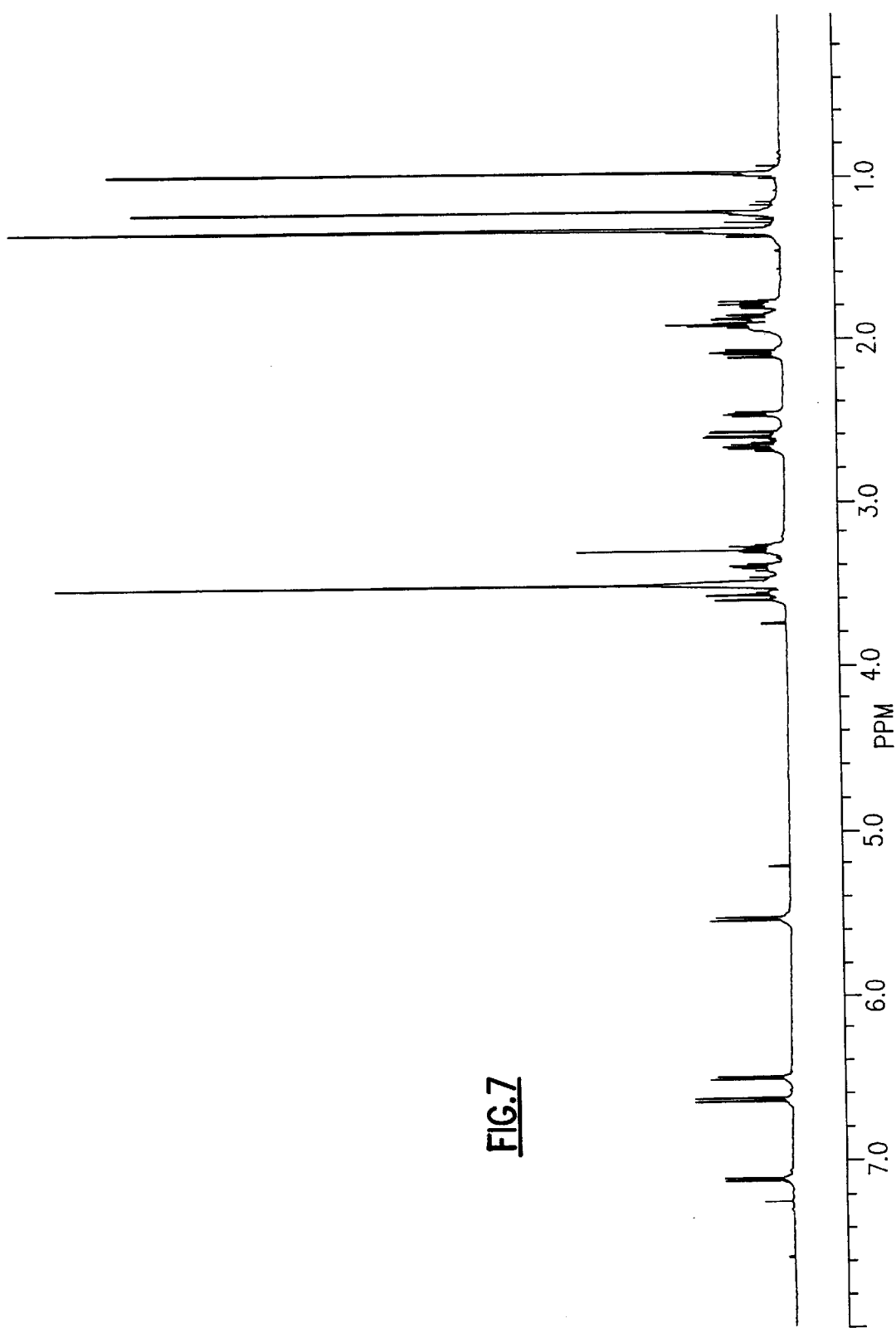
FIG. 7 shows the $^1$H-NMR spectrum of stephacidin A in CH$_3$OD/CDCl$_3$ (1:1).

| | |
|---|---|
| Description: | white amorphous solid |
| Molecular Formula: | $C_{26}H_{29}O_3N_3$ |
| Molecular Weight: | 431 |
| Mass Spectrum: | HR-ESIMS ion: 432.2292 $[M + H]^+$ Positive ESI-MS ions: 449 $[M + NH_4]^+$ Negative ESI-MS ions: 430$[M - H]^-$ |
| Ultraviolet Spectrum | $\lambda$ max $_{MeOH}$ (log $\epsilon$) 211 (4.52), 242 (4.54), 309 (3.96), 335 (sh. 3.64) nm (FIG. 5). Sample dissolved in methanol at concentration of 0.0010 g/L. |
| Infrared Spectrum: | Major Bands ($cm^{-1}$) 3442, 2973, 2481, 1691, 1673, 1638, 1439, 1384, 1201, 1158,1120, 1075, 913, 808, 734 $cm^{-1}$ (FIG. 6) |
| $^1$H-NMR | $\lambda_H$ ($CDCl_3$/$CH_3OD$) in ppm, J in Hz (FIG. 7) 7.10 (1H, d, J = 8.4), 6.63 (1H, d, J = 9.7), 6.50 (1H, d, J = 8.4), 5.52 (1H, d, J = 9.7), 3.56 (H, d, J = 15.4), 3.38 (1H, m), 3.27 (1H, m), 2.65 (1H, m), 2.58 (1H, d, J = 15.4), 2.45 (1H, dd, J = 10.3, 4.7), 2.09 (1H, dd, J = 13.5, 10.3), 1.92 (2H, m), 1.84 (1H, dd, J = 13.5, 4.7), 1.78, (1H, m), 1.32 (6H, s), 1.21 (3H, s), 0.97 (3H, s) |

TABLE 2-continued

Physico-Chemical Properties of Stephacidin A

Figure 8:
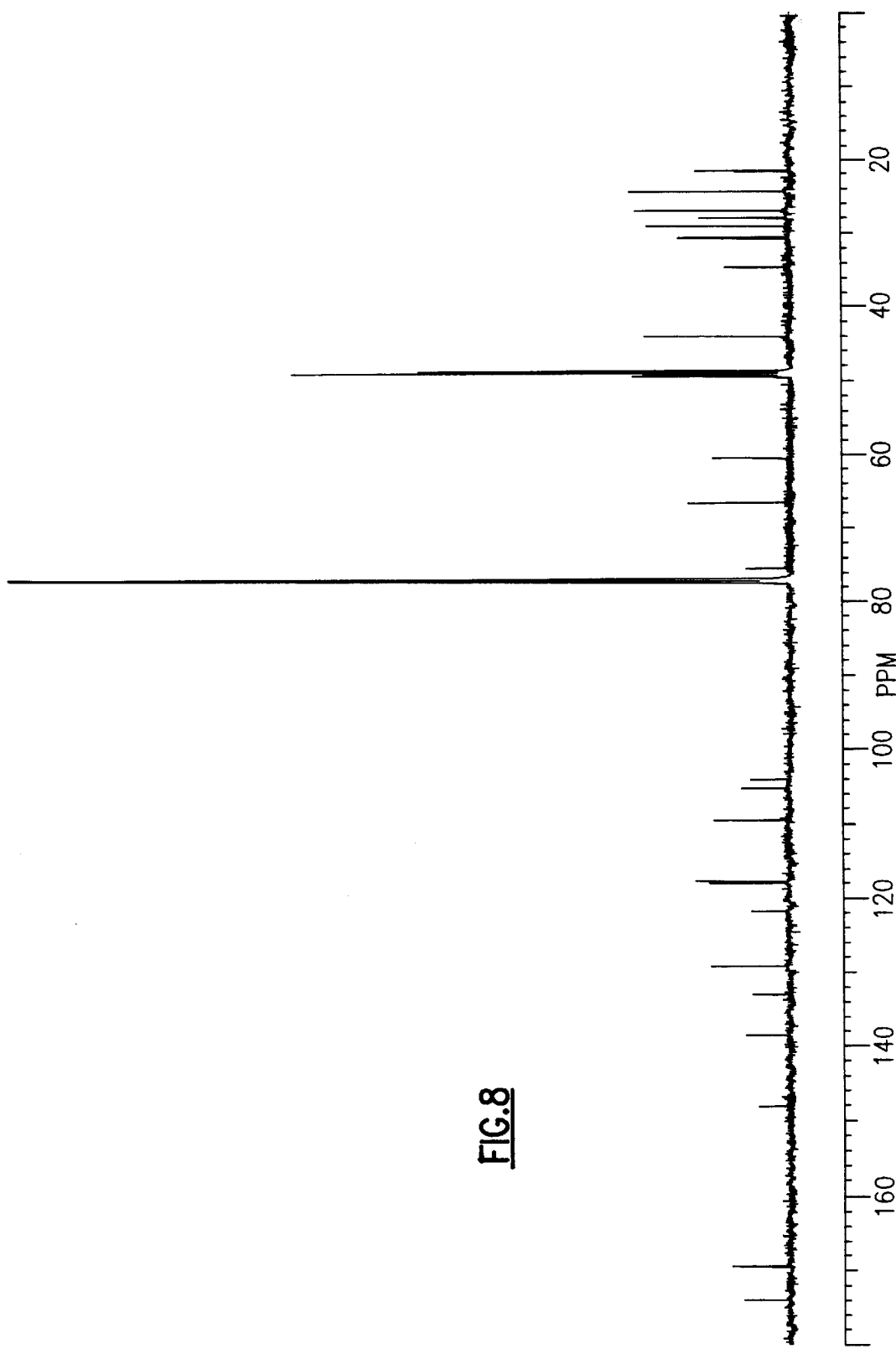
FIG. 8 shows the $^{13}$C-NMR spectrum of stephacidin A in CH$_3$OD/CDCl$_3$ (1:1).

| | |
|---|---|
| $^{13}$C-NMR | $\lambda_C$ (CDCl$_3$/MeOD) in ppm (FIG. 8) 174.0, 169.3, 148.1, 138.6, 133.0, 129.1, 121.6, 117.9, 117.5, 109.4, 105.1, 104.0, 75.4, 66.6, 60.3, 49.4, 43.9, 34.6, 30.7, 29.1, 27.9, 27.0, 27.0, 24.3, 24.3, 21.6 |

Based on the characterizing properties for the antibiotics, the structures of stephacidin A and B have been determined to be as follows:

Scheme 1
Structure of Stephacidin A and tentative structure of Stephacidin B

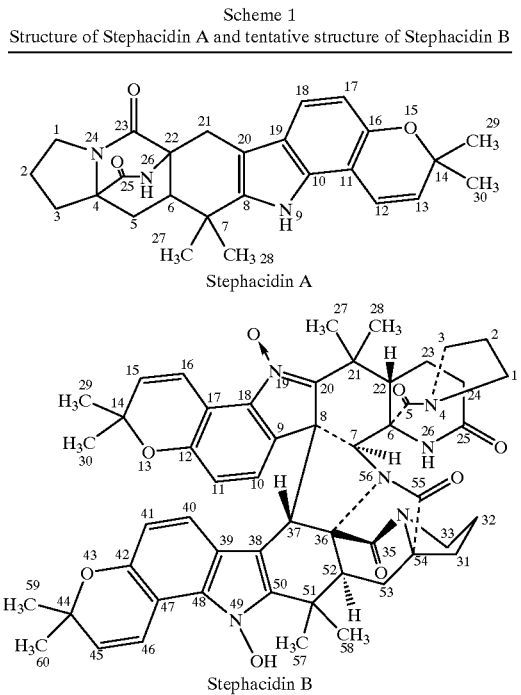

Stephacidin A

Stephacidin B

Both the stephacidin A (monomer) and stephacidin B (dimer) can form pharmaceutically acceptable salts with nontoxic organic or inorganic acids and such salts are encompassed within the term "stephacidin A" and "stephacidin B" as used herein. For example, stephacidin A can be converted to a hydrochloride salt by treatment with hydrochloric acid to yield a water-soluble hydrochloride salt at an amino group such as 9NH. Similarly, stephacidin B can form acid addition salts at amino groups. Other examples of suitable acids for salt formation include hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic.

The stephacidin A and B compounds may also form pharmaceutically acceptable amide derivatives by treatment with standard acylation reagents such as acetic acid anhydride to convert amino groups to amide groups. Such acylation reaction may be carried out in the presence of an organic base in an inert organic solvent, e.g. 4-dimethylaminopyridine (DMAP) and triethylamine in methylene chloride. It is intended that the term "stephacidin A and B" as used herein includes such pharmaceutically acceptable amide derivatives within its scope.

Biological Properties:

In Vitro Cytotoxicity

Stephacidin A demonstrated potent in vitro cytotoxicity against several human tumor cell lines (see Table 3 below). Stephacidin A was 10-fold less potent but within our in vivo criteria for acceptable activity. Good selectivity was observed in the testosterone dependent LNCaP cells, especially with stephacidin B. The effects of this compound are not mediated by p53, mdr or bcl2, and it is not tubulin or topoisomerase II mediated, indicating a novel mechanism of action.

TABLE 3

In vitro cytotoxicity of Stephacidin A and Stephacidin B

| Cell Line | Histotype | Characteristic | IC$_{50}$ ($\mu$M) Stephacidin B | IC$_{50}$ ($\mu$M) Stephacidin A |
|---|---|---|---|---|
| A2780 | Ovarian | Parental | .33 | 4.0 |
| A2780/DDP | Ovarian | mutp53/bcl2+ | .43 | 6.8 |
| A2780/Tax | Ovarian | Taxol resistant | .26 | 3.6 |
| PC3 | Prostate | Testosterone independent | .37 | 2.1 |
| LNCaP | Prostate | Testosterone sensitive | .06 | 1.0 |
| HCT116 | Colon | Parental | .46 | 2.1 |
| HCT116/mdr+ | Colon | Overexpresses Mdr+ | .46 | 6.7 |
| HCT116/Topo | Colon | Resistant to to etoposide | .42 | 13.1 |
| MCF-7 | Breast | Estradiol sensitive | .27 | 4.2 |
| SKBR3 | Breast | Estradiol-independent | .32 | 2.15 |
| LX-1 | Lung | Sensitive | .38 | 4.22 |

The in vitro cytoxicity assay used for the data above was carried out as follows:

In Vitro Cytotoxicity Assay

In vitro cytotoxicity was assessed in human carcinoma cells by the MTS (3-(4,5-dimethylthiazol-2-yl)-5-(3-carboxymethoxyphenyl)-2-(4 -sulphenyl)-2H-tetrazolium, inner salt) assay (5). Cells were plated at 4,000 cell/well in 96 well microtiter plates and 24 hours later drugs were added and serial diluted. The cells were incubated at 37° form 72 hours at which time the tetrazolium dye, MTS at 333 µg/ml (final concentration), in combination with the electron coupling agent phenazine methosulfate at 25 µM (final concentration) was added. A dehydrogenase enzyme in live cells reduces the MTS to a form that absorbs light at 492 nm which can be quantitated spectrophotometrically. The greater the absorbance the greater the number of live cells. The results are expressed as an $IC_{50}$, which is the drug concentration required to inhibit cell proliferation (i.e. absorbance at 492 nm) to 50% of that of untreated control cells.

Apoptosis Induction

Table 4 below shows that both stephacidin B and stephacidin A are potent inducers of apoptosis in both testosterone sensitive (LNCaP) and independent cells (A2780). These results suggest two independent mechanisms of action or one mechanism that is more essential to cells when testosterone sensitivity is expressed.

TABLE 4

Effect of Stephacidin B and Stephacidin A

| Compounds | Control | 0.1 x | 1 x | 5 x | 10 x | 20 x |
|---|---|---|---|---|---|---|
| % of LNCaP Cells in Apoptosis Multiples of 72 hour cytotoxic IC50 | | | | | | |
| Stephacidin A | 0.06 | 0.02 | 0.00 | 0.15 | 5.75 | 11.81 |
| Stephacidin B | 0.00 | 0.02 | 0.00 | 0.05 | 4.52 | 11.13 |
| % of A2780 Cells in Apoptosis Multiples of 72 hour cytotoxic IC50 | | | | | | |
| Stephacidin A | 4 | 1 | .8 | 21 | 14 | 15 |
| Stephacidin B | .8 | .5 | .2 | 1.0 | 33 | 5 |

The apoptosis assay used for the data above was carried out as follows:

Apoptosis Determination

Cells were plated, incubated overnight, treated with compound for 24 hours then harvested by trypsinization. For cell cycle analysis cells were trypsinized, permeated, stained with 50 ug/ml propidium iodide and analyzed by FACS. For apoptosis evaluation (TUNEL assay) cells were permeated and reacted with TdT and fluoresceinated dUTP for 3 hours following the procedure recommended by the APO-Direct kit (Pharmingen).

As indicated above, stephacidin A and B demonstrate inhibitory activity against mammalian tumors, particularly prostate carcinoma. Thus, in another aspect of the present invention, there is provided a method for therapeutically treating a mammalian host affected by a malignant tumor sensitive to stephacidin A and/or B which comprises administering to said host an effective tumor-inhibiting dose of stephacidin A or stephacidin B.

In yet another aspect of the present invention, a pharmaceutical composition is provided which comprises an effective tumor-inhibiting dose of stephacidin A or B in combination with an inert pharmaceutically acceptable carrier or diluent.

The pharmaceutical compositions may contain other active antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other suitable sterile injectable medium immediately before use.

For use as an antitumor agent, optimal dosages and regimens of the stephacidin A and B antibiotics can be readily ascertained by those skilled in the art. It will, of course, be appreciated that the actual dose of compound used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and nature and severity of the disease.

The following example is provided for illustrative purposes only and is not intended to limit the scope of the invention. Volume ratios used in the present application, unless otherwise indicated, are volume/volume. The following abbreviations are used in the specification and drawings:

MeOH=methonol
EtOAc=ethyl acetate
General Methods:

Analytical Thin Layer Chromatography (TLC)

Silica gel precoated thin layer chromatography plates, Kieselgel 60 F254 on aluminum sheet, 5×20 cm, 0.2 mm, were purchased from EM Separations, Gibbstown, N.J. The plates were developed in a tank equilibrated with methylene chloride/methanol (49:4 v/v). The components of the resulting chromatogram were detected under a UV light, and visualized by phosphomolybidic acid followed by prolonged heating.

Preparative TLC

Silica gel precoated Kieselgel 60 F254 plates on glass, 20×20 cm, 2 mm, purchased from EM Separations, were used for preparative purification. The plates were developed in a tank equilibrated with methylene chloride/methanol (49:4 v/v). The components of the resulting chromatogram were detected under a UV light. The silica bands containing the components were scraped and pressed to a fine powder, followed by elution with chloroform/methanol (3:1, v/v). The eluant was then evaporated in vacuo to dryness.

Analytical HPLC

The purification of stephacidin B and stephacidin A was monitored by HPLC analysis on a Microsorb-MV 5 µC-18 column, 4.6 mm i.d.×25 cm l. (Rainin Instrumnet Company, Inc., Woburn, Mass.). Analyses were done on a Hewlett Packard 1090 Liquid Chromatograph, equipped with a model photodiode array spectrophotometer set at 254 and 280 nm, and HPLC$^{3D}$ ChemStation operating software. A gradient solvent system and 0.01 M potassium phosphate buffer (PH 3.5) was used, according to the method of D. J. Hook et al (J. Chromatogr. 385, 99, 1987). The eluant was pumped at a flow rate of 1.2 ml/min.

Preparative HPLC

The following components were used to construct a preparative HPLC system: Dynamax SD-200 pumps, Dynamax dual wavelength spectrophotometer UV-D11 and Dynamax method manager software, a Microsorb-MV 5 $\mu$C-18 column, 10 mm i.d.×25 cm l, plus 10 mm i.d.×5 cm l. guard column (Rainin Instrumnet Company, Inc., Woburn, Mass.). A gradient solvent system consisting of acetonitrile and water, were used at a flow rate of 5 ml/min with run time of 32 minutes. The compounds were detected by monitoring the eluate stream at 254 nm.

Analytical Instrumentation

Low resolution MS measurements were performed with a Finnigan MAT 900 magnetic sector mass spectrometer, using the positive electrospray ionization mode. MS/MS measurements were conducted with Finnigan LCQ (ion trap MS) with electrospray as ionization mode. High resolution MS data were determined with a Finnigan MAT 900 magnetic sector mass spectrometer, positive electrospray ionization mode, ppg reference. The UV spectra were obtained using a Hewlett-Packard 8452A diode array spectrophotometer. IR measurements were taken on a Perkin Elmer 2000 Fourier Transform spectrometer. $^1$H-NMR and $^{13}$C-NMR spectra were obtained on a Bruker AM-500 500 MHz instrument operating at 500.13 and 125.76 MHz, respectively, using a 5-mm broad-banded probe.

EXAMPLE 1

Preparation of Stephacidin A and B
A. Fermentation of the antibiotics

Fungal cultures of *Aspergillus ochraceus* ATCC-74432 were grown on potato-dextrose agar slants containing the following ingredients per liter of deionized water: potato infusion, 200 g; dextrose, 20 g; agar, 15 g. The slant cultures were allowed to grow for 7 days at 28° C. Glycerol/water solvate (15%, w/v) was added and spore suspensions were prepared, divided into aliquots, and frozen in a dry ice-acetone bath. The frozen spore suspensions so obtained were then stored at −80° C.

From the frozen spore suspensions, 0.1 ml was used to inoculate a potato-dextrose slant which was inoculated at 28° C. for 7 days. A spore suspension was made using 0.85% saline and the spore suspension was transferred onto a 24.5×24.5 cm. Nunc plate containing 250 ml of medium containing the following ingredients per liter of deionized water: soluble starch, 20 g;,dextrose, 5 g.; soybean meal, 10 g; corn steep liquor, 10 g; NZ-amine type A, 3 g.; sodium chloride, 3 g; calcium carbonate, 3 g; agar, 10 g. The culture was incubated at 28° C. Maximum production of the desired antibiotics was achieved after 7 days of incubation.
B. Isolation and Purification Preparation of Crude Extract A Each of 20 fermentation Nunc plates containing the culture grown on solid media was soaked with 200 ml of methanol and stayed at room temperature for two hours. The liquid layer was combined and concentrated to around 800 ml under a nitrogen stream to remove most of the methanol. Water was then added to bring the volume to approximately 1 liter. The aqueous solution was then partitioned three times with an equal volume of ethyl acetate in a separatory funnel. Stephacidin B and stephacidin A were concentrated in the ethyl acetate layer. The aqueous layer was removed. The organic layer was combined and then evaporated to dryness in vacuo in a rotary evaporator to 1.1 g of residue A.

Sephadex LH-20 Chromatography of Residue A

Residue A (1.1 g) was dissolved in 4 ml metanol and applied to a 3×100 cm Spectrum column packed with 200 g Sephadex LH-20 in metanol. The column was eluted with methanol. Fractions measuring 8–10 ml each were collected at a flow rate of 2–3 ml/min. Fractions were consolidated on the basis of silica TLC profiles (chloroform/methanol 9:1, phosphormolybdic acid spray). In this manner, seven groups of fractions were obtained. Analytical HPLC analyses indicated that the second group of fractions (Residue B, 460 mg) and the third fraction (Residue C, 250 mg) contained stephacidin B and stephacidin A, respectively.

Preparative HPLC of Residue B (Isolation of Stephacidin B)

Final purification of stephacidin B from Residue B could be achieved by using the specified Rainin Dynamax preparative HPLC system. A typical injection sample size was 5 mg/0.2 ml methanol. Elution flow rate was 5 ml/min. Detection (UV) was at 254 nm. One hundred mg of Residue B was purified with the following solvent gradient:

| Time (min) | acetonitrile (%) | water (%) |
| --- | --- | --- |
| 0.00 | 30 | 70 |
| 32.00 | 85 | 15 |
| 37.00 | 30 | 70 |

The peak at 21.4 was collected and the solvent removed in vacuo to yield 10 mg pure stephacidin B.

Preparative TLC of Residue B (Isolation of Stephacidin B)

Preparative TLC was proven to be an alternative and more efficient way to purify stephacidin B from Residue B. 300 mg of Residue B was dissolved in 10 ml of methylene chloride-methanol 4:1. The solution was concentrated under a nitrogen stream to a final volume of 2 ml, and then applied to four Silica gel precoated Kieselgel 60 F254 plates on glass, 20×20 cm, 2 mm, EM Separations. The plates were developed in a tank equilibrated with methylene chloride/methanol (49:4 v/v). The components of the resulting chromatogram were detected under a UV light. The silica bands containing the components (Rf 0.84) were scraped and pressed to a fine powder, followed by elution with chloroform/methanol (3:1, v/v). The eluant was then evaporated in vacuo to give 75 mg of stephacidin B.

Sephadex LH-20 Chromatography of Residue C

Residue C (250 mg) was further purified again using Sephadex LH-20 column chromatography (3×100 cm Spectrum column packed with 200 g Sephadex LH-20 in metanol, eluted with methanol) Fractions measuring 8–10 ml each were collected at a flow rate of 2–3 ml/min. Fractions were consolidated on the basis of silica TLC profiles (chloroform/methanol 9:1, phosphormolybdic acid spray). In this manner, seven groups of fractions were obtained. Analytical HPLC analyses indicated that the second group of fractions (Residue D, 95 mg) contained stephacidin A.

Preparative TLC of Residue D (Isolation of Stephacidin A)

The final purification of stephacidin A from Residue C was achieved by preparative TLC. Ninty five mg of Residue D was dissolved in 5 ml of methylene chloride-methanol 4:1. The solution was concentrated under a nitrogen stram to a final volume of 1 ml, and then applied to two Silica gel precoated Kieselgel 60 F254 plates on glass, 20×20 cm, 2 mm, EM Separations. The plates were developed in a tank equilibrated with methylene chloride/methanol (49:4 v/v). The components of the resulting chromatogram were detected under a UV light. The silica bands containing the components (Rf 0.64) were scraped and pressed to a fine powder, followed by elution with chloroform/methanol (3:1, v/v). The eluant was then evaporated in vacuo to give 15 mg of stephacidin A.

We claim:
1. The compound, stephacidin A having the formula

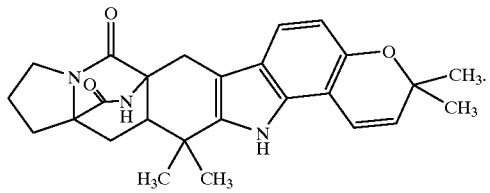

2. The compound stephacidin B having the formula

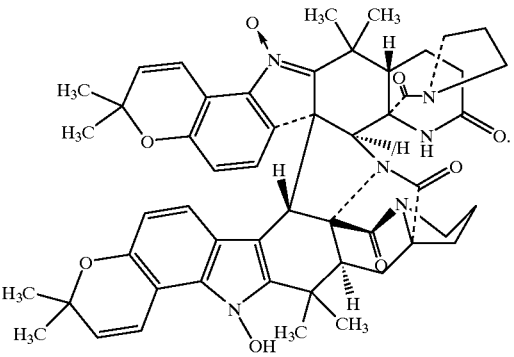

3. A pharmaceutical composition comprising an effective tumor-inhibiting amount of stephacidin A or stephacidin B in combination with a pharmaceutically acceptable carrier or diluent.

4. A method for inhibiting the growth of malignant tumors selected from ovarian, prostate, colon, breast and lung carcinomas in a mammalian host which comprises administering to said host an effective tumor-inhibiting amount of stephacidin A or stephacidin B.

5. The method of claim 4 wherein the tumor is prostate carcinoma.

* * * * *